United States Patent [19]

Takiguchi et al.

[11] Patent Number: 4,798,777
[45] Date of Patent: Jan. 17, 1989

[54] ELECTROPHOTOGRAPHIC MEMBER CONTAINING VINYLENE BENZOCARAZOLE AS CHARGE TRANSPORTING MATERIAL

[75] Inventors: Takao Takiguchi, Tokyo; Masakazu Matsumoto; Toshihiro Kikuchi, both of Yokohama, all of Japan

[73] Assignee: Canon Kabushiki Kaisha, Tokyo, Japan

[21] Appl. No.: 14,855

[22] Filed: Feb. 13, 1987

[30] Foreign Application Priority Data

Feb. 19, 1986 [JP] Japan .................. 61-034775

[51] Int. Cl.$^4$ .............................. G03G 5/10
[52] U.S. Cl. .......................... 430/59; 430/84
[58] Field of Search .......... 430/58, 59, 57, 84, 430/79; 528/248, 422

[56] References Cited

U.S. PATENT DOCUMENTS 4,264,695 4/1981 Kozima et al. ............. 430/58
4,361,637 11/1982 Stofko et al. ............... 430/58

FOREIGN PATENT DOCUMENTS 2121789 1/1984 United Kingdom .

*Primary Examiner*—John L. Goodrow
*Attorney, Agent, or Firm*—Fitzpatrick, Cella, Harper & Scinto

[57] ABSTRACT

An electrophotographic photosensitive member which comprises a layer containing a compound represented by the formula (1) shown below:

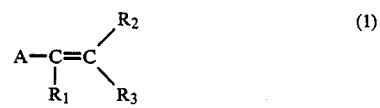

wherein A represents 1,2-, 2,3- or 3,4-benzocarbazolyl group; $R_1$, $R_2$ and $R_3$, which may be the same or different, each represent hydrogen atom, alkyl group, aralkyl group, aryl group or heterocyclic group, with proviso that $R_2$ and $R_3$ cannot be hydrogen atoms at the same time.

12 Claims, No Drawings

ELECTROPHOTOGRAPHIC MEMBER CONTAINING VINYLENE BENZOCARAZOLE AS CHARGE TRANSPORTING MATERIAL

BACKGROUND OF THE INVENTION

1. Field of the Invention

This invention relates to an electrophotographic photosensitive member, particularly to an electrophotographic photosensitive member having a low molecular weight organic photoconductive material which can give improved electrophotographic characteristics.

2. Description of the Related Art

In the prior art, as the photoconductive material to be used in electrophotographic photosensitive member, inorganic photoconductive materials such as selenium, cadmium sulfide, zinc oxide have been known. These photoconductive materials, while having a number of advantages such as chargeability to an appropriate potential in a dark place, small dissipation of charges in a dark place or rapid dissipation of charges by photoirradiation, also have various drawbacks. For example, in a selenium type photosensitive member, crystallization progresses readily by such factors as temperature, humidity, dust, pressure, etc., particularly crystallization occurs remarkably when the atmosphere temperature exceeds 40° C., whereby such drawbacks as lowering in chargeability or generation of white speckles in the image are involved. A cadmium sulfide type photosensitive member cannot obtain stable sensitivity under a humid environment and a zinc oxide type photosensitive member requires sensitization effect with a sensitizing dye typically by Rose Bengal. However, such a sensitizing dye is subject to charging deterioration by corona charging or light fading by exposed light, whereby there is the drawback that no stable image can be given for a long term.

On the other hand, various organic photoconductive polymers typically polyvinylcarbazole have been proposed. These polymers, although excellent in film forming characteristic, lightweight, etc., as compared with the inorganic type photoconductive materials as described above, have been practically applied only with much difficulty up to date. This is because no satisfactory film forming characteristic has been obtained yet, and also it is inferior in respect of sensitivity, durability and stability with environmental change as compared with inorganic type photoconductive materials. Also, there have been proposed low molecular weight organic photoconductive materials such as hydrazone compounds as disclosed in U.S. Pat. No. 4,150,987, triarylpyrazoline compounds as disclosed in U.S. Pat. No. 3,837,851 9-styrylanthracene compounds as disclosed in Japanese Patent Laid-open Publications Nos. 94828/1976 and 94829/1976. Such a low molecular weight organic photoconductive material has overcome the drawback of film forming characteristic which has been the problem in the field of organic photoconductive polymers by selecting suitably a binder to be used, but it cannot be said to be satisfactory with respect to sensitivity.

For such reasons as mentioned above, in recent years, a laminated structure having the photosensitive layer separated in function into the charge generation layer and the charge transport layer has been proposed. An electrophotographic photosensitive member having the laminated structure as the photosensitive layer can be improved with respect to sensitivity to visible light, charge retentive force, surface strength, etc. Such electrophotographic photosensitive members are disclosed in, for example, U.S. Pat. Nos. 3,837,851 and 3,871,882.

However, in the electrophotographic photosensitive member by use of a low molecular weight organic photoconductive material of the prior art in the charge transport layer, sensitivity characteristics are not necessarily satisfactory, and also fluctuations at the light portion potential and the dark portion potential are great when repeated charging and exposure are performed. Thus, there remain some points to be improved.

SUMMARY OF THE INVENTION

An object of the present invention is to provide an electrophotographic photosensitive member which has met the drawbacks or disadvantages as described above.

Another object of the present invention is to provide a novel organic photoconductive member.

A further object of the present invention is to provide a novel charge transporting substance in the laminated type photosensitive layer having the functions separated into the charge generation layer and the charge transport layer.

Still another object of the present invention is to provide an electrophotographic photosensitive member with high sensitivity which is excellent in potential stability.

According to the present invention, there is provided an electrophotographic photosensitive member comprising a layer containing a compound represented by the formula (1) shown below:

wherein A represents 1,2-, 2,3- or 3,4-benzocarbazolyl group; $R_1$, $R_2$ and $R_3$, which may be the same or different, each represent hydrogen atom, alkyl group, aralkyl group, aryl group or heterocyclic group, with proviso that $R_2$ and $R_3$ cannot be hydrogen atoms at the same time.

Such objects of the present invention can be accomplished by an electrophotographic photosensitive member having a layer containing a compound represented by the formula (1) shown below.

In the above formula, A represents 1,2-, 2,3- or 3,4-benzocarbazolyl group, particularly preferably a 1,2-benzocarbazolyl group as shown by the formula (2). The benzocarbazolyl group in the formula (1) and (2) may have substituents.

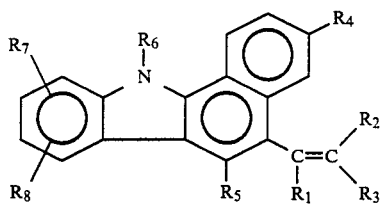

(2)

Further, when A is a 1,2-benzocarbazolyl group, $R_2$ and $R_3$ should preferably be phenyl groups as shown by the formula (3). The phenyl group may have substituents.

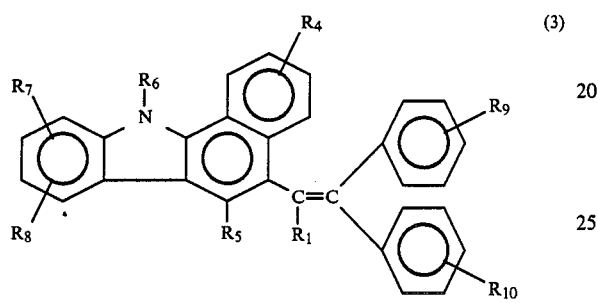

(3)

Here, in the formula, $R_1$ and $R_6$ each represents hydrogen atom or alkyl group such as methyl, ethyl, propyl, etc., or an aralkyl group which may have substituent such as benzyl, phenethyl, naphthylmethyl, etc., or an aryl group which may have substituent such as phenyl, naphthyl, anthryl, etc., or heterocyclic group which may have substituent such as pyridyl, quinolyl, thienyl, furyl, etc. In the formula, $R_4$, $R_5$, $R_7$, $R_8$, $R_9$ and $R_{10}$ each represent hydrogen atom, an alkyl group such as methyl, ethyl, propyl, etc., or an alkoxy group such as methoxy, ethoxy, propoxy, etc., or a halogen atom such as fluorine, chlorine, bromine, etc., or a substituted amino group such as dimethylamino, diethylamino, etc., or an alkylthio group such as methylthio, ethylthio, etc. Here, as the preferable substituents which may be possessed when $R_1$, $R_6$ are aralkyl group or aryl group or heterocyclic group, alkyl groups, alkoxy groups, halogen atoms, aryloxy groups, substituted amino groups and alkylthio groups shown for $R_4$, $R_5$, $R_7$, $R_8$, $R_9$ and $R_{10}$ may be included.

DETAILED DESCRIPTION OF THE INVENTION

It is considered that the benzocarbazole type styryl compound to be used in the present invention is remarkably improved in the characteristic as the charge transporting material by having a fused benzene ring imparted to the carbazole. That is, the injection of the hole from the charge generating material is facilitated by the decrease of the ionization potential resulting from the expansion of the $\pi$ electron conjugated system. Further, movement or transfer of the charge between molecules become easy by the increase of the overlap between the molecules.

In the following, typical examples of the compounds represented by the above formula shown.

-continued

Exemplary compounds

| No. | Structure |
|---|---|
| I-9 | N-benzyl carbazole with -CH=C(phenyl)₂ substituent |
| I-10 | 9-ethyl-3-(methylthio)carbazole with -C(CH₃)=C(phenyl)₂ substituent |
| I-11 | 9-ethyl-3-(diethylamino)carbazole with -CH=C(phenyl)₂ substituent |
| I-12 | 9-n-butyl-methoxycarbazole with -CH=C(phenyl)₂ substituent |
| I-13 | 9-n-propylcarbazole with -CH=C(2-furyl)₂ substituent |
| I-14 | 9-n-butyl-chlorocarbazole with -CH=C(phenyl)₂ substituent |
| I-15 | 9-(4-chlorophenyl)carbazole with -CH=C(phenyl)₂ substituent |
| I-16 | 9-n-butyl-methoxycarbazole with -CH=C(phenyl)₂ substituent |
| I-17 | N-(pyridyl)carbazole with -CH=C(4-ethoxyphenyl)₂ substituent |
| I-18 | 9-n-octylcarbazole with -C(phenyl)=C(phenyl)₂ substituent |
| I-19 | 9-n-pentylcarbazole with -CH=C(3-fluorophenyl)₂ substituent |
| I-20 | 9-phenylcarbazole with -CH=C(3-methoxyphenyl)₂ substituent |
| I-21 | 9-n-propyl-ethoxycarbazole with -CH=C(phenyl)₂ substituent |
| I-22 | 9-n-butyl-(ethylthio)carbazole with -CH=C(phenyl)₂ substituent |
| I-23 | 9-n-hexylcarbazole with -C(phenyl)=C(phenyl)(CH₂-phenyl) substituent |

-continued

Exemplary compounds

| No. | Structure |
|---|---|
| I-24 | N-(n-C₃H₇) carbazole with SCH₃ substituent, CH=C(phenyl)₂ |
| I-25 | N-(n-C₄H₉) carbazole with Cl substituent, CH=C linked to bis(OC₂H₅)phenyl |
| I-26 | N-(CH₂-C₆H₄-OCH₃) carbazole, CH=C linked to bis(OCH₃)phenyl |
| I-27 | N-(n-C₆H₁₃) carbazole with Cl substituent, CH=C linked to bis(Cl)phenyl |
| I-28 | N-(n-C₆H₁₃) carbazole, C=C(phenyl)₂ with CH₂-C₆H₄-OCH₃ |
| I-29 | N-(n-C₆H₁₃) carbazole, CH=C linked to bis(H₃CO)phenyl |
| I-30 | N-(n-C₄H₉) carbazole with OCH₃ and H₃CO substituents, CH=CH-phenyl |
| I-31 | N-(n-C₄H₉) carbazole with H₃CS and SCH₃ substituents, CH=CH-phenyl |
| I-32 | N-(C₂H₅) carbazole with OCH₃ substituent, CH=CH-phenyl |
| I-33 | N-(C₂H₅) carbazole with H₃CO substituent, CH=C linked to bis(OCH₃)phenyl |
| I-34 | N-(n-C₅H₁₁) carbazole with OC₂H₅ substituent, CH=CH-phenyl |
| I-35 | N-(n-C₄H₉) tetrahydrocarbazole with OC₂H₅ substituent, CH=CH-phenyl |
| I-36 | N-(C₂H₅) carbazole with H₅C₂O substituent, CH=CH-phenyl |
| I-37 | N-(n-C₅H₁₁) carbazole with H₅C₂O substituent, CH=CH-phenyl |
| I-38 | N-(iso-C₃H₇) carbazole with N(CH₃)₂ substituent, CH=CH-phenyl |
| I-39 | N-(C₂H₅) carbazole with N(CH₃)₂ substituent, CH=CH-phenyl |

-continued

Exemplary compounds

| No. | Structure |
|---|---|
| I-40 | N-substituent: n-C₆H₁₃; with C=CH-naphthyl substituent |
| I-41 | N-substituent: n-C₄H₉; H₃C- on ring; C=CH(phenyl)₂ |
| I-42 | N-substituent: n-C₄H₉; OCH₃ on ring; C=CH(phenyl)₂ |
| I-43 | N-substituent: n-C₄H₉; OCH₃ on ring; C=CH(phenyl)₂ |
| I-44 | N-substituent: n-C₂H₅; H₃C- on ring; C=CH(phenyl)₂ |
| I-45 | N-substituent: n-C₆H₁₃; OCH₃ on ring; C=CH(phenyl)₂ |
| I-46 | N-substituent: n-C₄H₃; H₃C, H₃C on ring; CH₃; C=CH(phenyl)₂ |
| I-47 | N-substituent: C₂H₅; H₃C, H₃C, OCH₃ on ring; C=CH(phenyl)₂ |

In the following, Synthesis examples of the above compounds are shown. Synthesis Example (Synthesis of the Exemplary Compound No. I-6)

1,2-benzo-3,4-dihydrocarbazole synthesized from phenylhydrazine and α-tetralone according to the method of J. Am. Chem. Soc., 69, 2910 (1947) was dehydrogenized with palladiumcarbon to obtain 1,2-benzocarbazole.

To a solution of 6.5 g (29.9 mmol) of 1,2-benzocarbazole dissolved in 65 ml of DMF, 1.82 g (45.5 mmol) of oily sodium hydride (content 60%) was added portionwise at room temperature under stirring, and the mixture was stirred after completion of the addition at room temperature for 20 minutes. Then, 5.20 ml (47.4 mmol) of n-butyl iodide was slowly added dropwise, and the mixture was stirred after completion of the dropwise addition at room temperature for 1 hour. After the reaction, the reaction product was pored into 250 ml of water, extracted with ethyl acetate, the organic layer was washed with water and dried over Glauber's salt, followed by drying under reduced pressure. The crystals of N-n-butyl-1,2-benzocarbazole precipitated by addition of a small amount methanol were collected by filtration. Amount obtained 7.89 g, yield 96.5%.

7.7 g (28.2 mmol) of N-n-butyl-1,2-benzocarbazole, 3.56 ml (28.9 mmol) of N-methylformanilide, 2.41 ml (25.8 mmol) of phosphorus oxychloride and 15 ml of o-dichlorobenzene were charged into a 100 ml four-necked flask and the mixture was stirred by heating at a temperature maintained at 90 to 100° C. for 4 hours. After completion of the reaction, the reaction product was poured into an aqueous sodium acetate solution, extracted with dichloromethane, the organic layer was washed with water and dried over Glauber's salt, followed by drying under reduced pressure. The residue was purified by recrystallization to obtain crystals of N-n-butyl-1,2-benzocarbazole-3-carboaldehyde. Amount obtained 4.67 g, yield 55.0%.

Into 15 ml of N,N-dimethylformamide was added 2.0 g (17.8 mmol) of potassium t-butoxide, and to the mixture was added dropwise at room temperature under stirring a solution of 3.0 g (9.95 mmol) of N-n-butyl-1,2-benzocarbazole-3-carboaldehyde and 4.3 g (14.1 mmol) of diethyl diphenylmethylphosphonate dissolved in 30 ml of N,N-dimethylformamide slowly as that the reaction temperature may not exceed 35° C. After completion of the dropwise addition, the mixture was stirred at room temperature for 4 hours. After completion of the reaction, the reaction product was poured into water, and the precipitated crystals were purified by recrystallization to give 2.70 g of N-n-butyl-1,2-benzo-3-(α-phenylstyryl)carbazole (exemplary compound No. I-6). m.p. 155°–156° C. Yield 60.1%.

| | Elemental analysis | |
|---|---|---|
| | Calcd. (%) | Found (%) |
| C | 90.43 | 90.38 |
| H | 6.47 | 6.52 |
| N | 3.10 | 3.08 |

Other exemplary compounds were also similarly synthesized.

In a preferable specific example of the present invention, the compound represented by the above formula can be used for the charge transporting material in the electrophotographic photosensitive member having the photosensitive layer separated in function into the charge generation layer and the charge transport layer.

The charge transport layer according to the present invention should be preferably formed by coating solution formed by dissolving the compound represented by the above formula and a binder in a suitable solvent, followed by drying. Examples of the binder used here may include polyarylated resin, polysulfone resin, polyamide resin, acrylic resin, acrylonitrile resin, methacrylic resin, vinyl chloride resin, vinyl acetate resin, phenol resin, epoxy resin, polyester resin, alkyd resin, polycarbonate, polyurethane or copolymer resins containing two or more of the repeating units of these resins such as styrene-butadiene copolymer, styrene-acrylonitrile copolymer, styrenemaleic acid copolymer, etc. Also, in addition to such insulating polymers, organic photoconductive polymers such as polyvinylcarbazole, polyvinylanthracene or polyvinylpyrene may be also used.

The formulation proportion of the binder resin and the compound of the present invention may be preferably 10 to 500 parts by weight of the compound of the present invention per 100 parts by weight of the binder.

The charge transport layer is electrically connected to the charge generation layer as described below, and has the function of receiving the charge carriers injected from the charge generation layer in the presence of an electrical field and also transporting these charge carriers to the surface. In this case, the charge transport layer may be laminated on the charge generation layer or alternatively therebeneath. However, it is desirable that the charge transport layer should be laminated on the charge generation layer. The charge transport layer is limited in capability of transporting charge carriers and therefore cannot be made thicker in film thickness than is necessary. Generally, it may be 5 μm to 30 μm, but preferable range is from 8 μm to 20 μm. The organic solvent to be used in forming such a charge transport layer may differ depending on the kind of the binder used, or it is preferable to select an organic solvent which does not dissolve the charge generation layer and the subbing layer as described below. Specific examples of organic solvent may include alcohols such as methanol, ethanol, isopropanol and the like; ketones such as acetone, methyl ethyl ketone, cyclohexanone and the like; amides such as N,N-dimethylformamide, N,N-diemthylacetamide and the like; sulfoxides such as dimethylsulfoxide and the like; ethers such as tetrahydrofuran, dioxane, ethylene glycol monomethyl ether and the like; esters such as methyl acetate, ethyl acetate and the like; aliphatic halogenated hydrocarbons such as chloroform, methylene chloride, dichloroethylene, carbon tetrachloride, trichloroethylene and the like; or aromatic compounds such as benzene, toluene, xylene, ligroine, monochlorobenzene, dichlorobenzene and the like.

Coating can be performed by use of the coating method such as dip coating, spray coating, spinner coating, bead coating, Meyer bar coating, blade coating, roller coating, curtain coating, etc. Drying may be preferably conducted according to the method in which heating drying is effected after drying at room temperature with finger touching. The heating drying may be performed at a temperature of 30° C. to 200° C. for a time within the range from 5 minutes to 2 hours either stationarily or under air stream.

The charge transport layer of the present invention can contain various additives. Examples of such additives may include diphenyl, diphenyl chloride, o-terphenyl, p-terphenyl, dibutyl phthalate, dimethyl glycol phthalate, dioctyl phthalate, triphenylphosphoric acid, methylnaphthalene, benzophenone, chlorinated paraffin, dilaurylthiopropionate, 3,5-dinitrosalicylic acid, various fluorocarbons, etc.

The charge generation layer to be used in the present invention can use another vapor deposition layer or a resin dispersion layer selected from charge generating substances such as selenium, selenium-tellurium, pyrylium, thiopyrylium, azulenium type dyes, phthalocyanine type pigments, anthoanthrone pigments, dibenzpyrenequinone pigments, pyranthrone pigments, azo pigments, indigo pigments, quinacridone type pigments, thiacyanine, nonsynmetric quinocyanine, quinocyanine or amorphous silicon described in Japanese Laid-open Patent Publication No. 143645/1979.

The charge generating substance to be used in the electrophotographic photosensitive member of the present invention may include inorganic compounds or organic compounds as shown below.

| Charge generating substance | |
|---|---|
| Amorphous silicon | II-1 |
| Selenium-tellurium | II-2 |
| Selenium-arsenic | II-3 |
| Cadmium sulfide | II-4 |

II-5

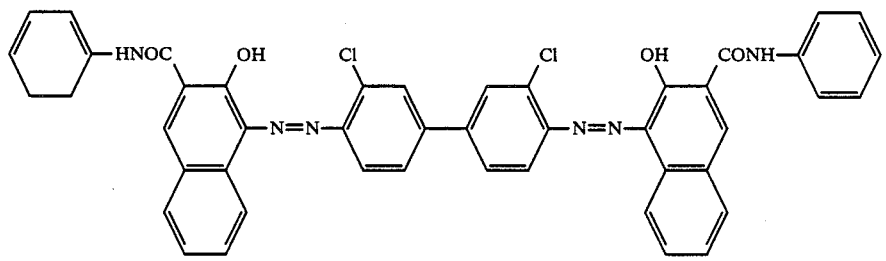

-continued
Charge generating substance

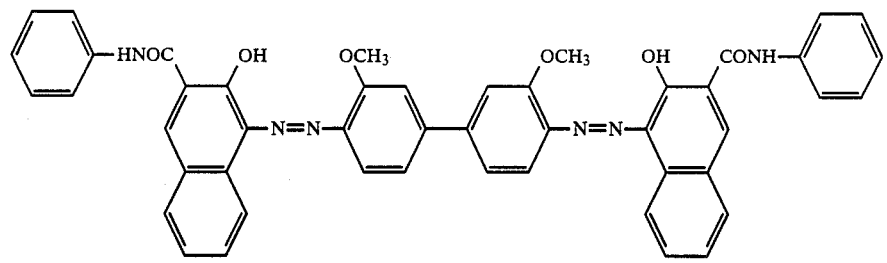

II-6

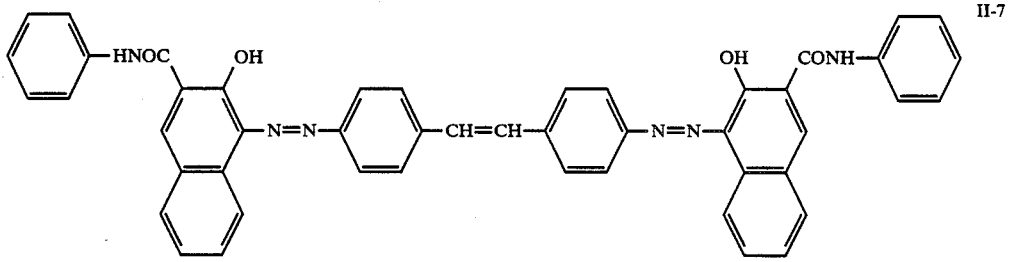

II-7

The charge generation layer can be formed by dispersing a charge generating substance as described above in a suitable binder and applying the dispersion on a substrate by coating, and it is also possible to obtain the charge generation layer by forming a vapor deposited film by means of a vacuum vapor deposition device. The binder resin which can be used in formation of the charge generation layer by coating can be selected from a wide scope of insulating resins, and also selected from organic photoconductive polymers such as poly-N-vinylcarbazole, polyvinylanthracene or polyvinylprene. Preferably, there may be employed polyvinylbutyral, polyarylate (e.g. polycondensate of bisphenol A and phthalic acid, etc.), polycarbonate, polyester, phenoxy resin, polyvinyl acetate, acrylic resin, polyacrylamide resin, polyamide, polyvinylpyridine, cellulose type resin, urethane resin, epoxy resin, casein, polyvinyl alcohol, polyvinylpyrrolidone, etc. The content of the resin contained in the charge generation layer may be suitably 80 wt. % or less, preferably 40 wt. % or less. Examples of the organic solvents to be used during coating may include alcohols such as methanol, ethanol, isopropanol and the like; ketones such as acetone, methyl ethyl ketone, cyclohexanone and the like; amides such as N,N-dimethylformamide, N,N-dimethylacetamide and the like; sulfoxides such as dimethyl sulfoxide and the like; ethers such as tetrahydrofuran, dioxane, ethylene glycol monomethyl ether and the like; esters such as methyl acetate, ethyl acetate and the like; aliphatic halogenated hydrocarbons such as chloroform, methylene chloride, dichloroethylene, carbon tetrachloride, trichloroethylene and the like; aromatic compounds such as benzene, toluene, xylene, ligroine, monochlorobenzene, dichlorobenzene and the like.

Coating can be practiced by use of the coating methods such as dip coating, spray coating, spinner coating, bead coating, Meyer bar coating, blade coating, roller coating, curtain coating, etc.

The charge generation layer should preferably contain as much as possible of the above organic photoconductive material in order to obtain sufficient absorbance and also to be made into a thin film layer having a film thickness of, for example, 5 μm or less, preferably 0.001 μm to 1 μm in order to make shorter the flying path of the charge carriers generated. This is attributable to the fact that most of the dose of incident light is absorbed in the charge generation layer to form a large number of charge carriers and further to the fact that the charge carriers generated are required to be injected into the charge transport layer without deactivation by recombination or trap.

The photosensitive layer comprising a laminated structure of such charge generation layer and charge transport layer is provided on a substrate having an electroconductive layer. As the substrate having an electroconductive layer, there may be employed those in which the substrate itself has electroconductivity such as aluminum, aluminum alloy, copper, zinc, stainless steel, vanadium, molybdenum, chromium, titanium, nikkel, indium, gold, platinum, etc. Further, plastics (e.g. polyethylene, polypropylene, polyvinyl chloride, polyethylene terephthalate, acrylic resin, polyfluoroethylene, etc.) having a layer formed by coating according to the vacuum vapor deposition method of aluminum, aluminum alloy, indium oxide, tin oxide, indium oxide-tin oxide alloy, etc., substrates having electroconductive particles (e.g. aluminum powder, titanium oxide, tin oxide, zinc oxide, carbon black, silver particles, etc.) together with a suitable binder coated on plastic or electroconductive substrates as mentioned above, substrates of plastics or papers impregnated with electroconductive particles or plastics containing electroconductive polymers, etc., can be used. When the substrate is electroconductive, the electroconductive layer may not be laminated in some cases.

It is also possible to provide a subbing layer having the barrier function and the adhesion function between the electroconductive layer and the photosensitive layer. The subbing layer can be formed of casein, polyvinyl alcohol, nitrocellulose, ethyleneacrylic acid copolymer, polyamide (nylon 6, nylon 66, nylon 610, copolymerized nylon, alkoxymethylated nylon, etc.), polyurethane, gelatin, aluminum oxide, etc.

The subbing layer may have a film thickness appropriately of 0.1 μm to 5 μm, preferably 0.5 μm to 3 μm.

In the case when a photosensitive member having an electroconductive layer, charge generation layer and a charge transport layer laminated in this order is used, since the compound of the present invention is positive hole transportable, the surface of the charge transport layer is required to be negatively charged. When exposure is effected after charging, at the exposed portion, the positive holes formed in the charge generation layer are injected into the charge transport layer. Thereafter they reach the surface to neutralize the negative charges, whereby attenuation of the surface potential occurs to give rise to an electrostatic contrast between the unexposed portion and the exposed portion. During developing, contrary to the case of using a charge transport material, it is necessary to use a positively charged toner.

In another specific example of the present invention, the disazo pigments as described above or pigments or dyes having photoconductivity such as pyrylium dyes, thiapyrylium dyes, selenapyrylium dyes, benzopyrylium dyes, benzothiapyrylium dyes, naphthopyrylium dyes, naphthothiapyrylium dyes as disclosed in U.S. Pat. Nos. 3,554,745, 3,567,438, 3,586,500, etc., may be also used as the sensitizer.

Also, in another specific example, an eutectic complex of a pyrylium dye and an electrically insulating polymer having an alkylidenediarylene moiety as disclosed in U.S. Pat. No. 3,684,502 may be also used as the sensitizer. The eutectic complex can be obtained as particulate eutectic complex by, for example, dissolving 4-[4-bis-(2-chloroethyl)aminophenyl]-2,6-diphenylthiapyryliumperchlorate and a poly(4,4'-isopropylidenediphenylenecarbonate) in a halogenated hydrocarbon solvent (e.g. dichloromethane, chloroform, carbon tetrachloride, 1,1-dichloroethane, 1,2-dichloroethane, 1,1,2-trichloroethane, chlorobenzene, bromobenzene, 1,2-dichlorobenzene) and then adding a non-polar solvent (e.g. hexane, octane, decane, 2,2,4-trimethylbenzene, ligroine). In the electrophotographic photosensitive member in this specific example, styrenebutadiene copolymer, silicone resin, vinyl resin, vinylidene chloride-acrylonitrile copolymer, styreneacrylonitrile copolymer, vinyl acetate-vinyl chloride copolymer, polyvinylbutyral, polymethyl methacrylate, poly-N-butyl methacrylate, polyesters, cellulose esters, etc., can be the binder.

The electrophotographic photosensitive member of the present invention is utilizable not only in electrophotographic copying machines, but can be also used widely for electrophotographic application fields such as laser printer, LED printer, CRT printer and electrophotographic print manufacturing systems.

According to the present invention, a high sensitivity electrophotographic photosensitive member can be made, and also the electrophotographic photosensitive member has the advantage of small fluctuation at the light portion potential and the dark portion potential when repeated charging and exposure are practiced.

The present invention is described below by referring to Examples.

EXAMPLE 1

A mixture of 7 g of a pigment obtained by successively refluxing a β-type copper phthalocyanine produced by Toyo Ink Seizo K.K. (trade name, Lionol Blue NCB Toner) in water, ethanol and benzene, followed by purification by filtration, 7 g of the resulting pigment, 14 g of Polyester Adhesive 49000 (solid 20%) (trade name), (produced by Du Pont Co.), 35 g of toluene and 35 g of dioxane was dispersed in a ball mill for 6 hours to prepare a coating liquid. The coating liquid was applied with Meyer bar on an aluminum sheet to a dried film thickness of 0.5 μm to prepare a charge generation layer.

Next, 7 g of the above exemplary compound No. I-6 as the charge transporting compound and 7 g of a polycarbonate resin (trade name "Panlite K-1300" produced by Teijin Kasei K.K.) were dissolved in a solvent mixture of 35 g of tetrahydrofuran and 35 g of chlorobenzene under stirring. The resultant solution was applied with Meyer bar on the above charge generation layer to a dried film thickness of 11 μm to prepare an electrophotographic photosensitive member having a photosensitive layer having two layer structures.

The electrophotographic photosensitive member thus prepared was subjected to corona charging at −5KV according to the static system by means of an electrostatic copying paper testing device Model-SP-428 produced by Kawaguchi Denki K.K., and after maintained in a dark place for 1 second, the charging characteristic was examined by exposure at a luminance of 2.5 lux.

As the charging characteristics, surface potential ($V_0$) and dosage ($E\frac{1}{2}$) necessary for attenuating the potential after dark decay for 1 sec. ($V_1$) to ½ were measured.

Further, for measuring the fluctuation at the light portion potential and the dark portion potential when used repeatedly, the photosensitive member prepared in this Example was plastered on the cylinder for photosensitive drum of the PPC copying machine NP-150Z produced by Canon K.K. and 50000 sheets of copying was performed with the same machine, and the fluctuations at the light portion potential ($V_L$) and at the dark portion potential ($V_D$) at the initial stage and after copying of 50000 sheets were measured.

Also, in place of the above exemplary compound, a compound of the following structural formulae (a), (b) and (c) was used to prepare a comparative sample-1, 2 and 3 according to entirely the same procedure, which was also subjected to the same measurement. These results are shown in the following Table.

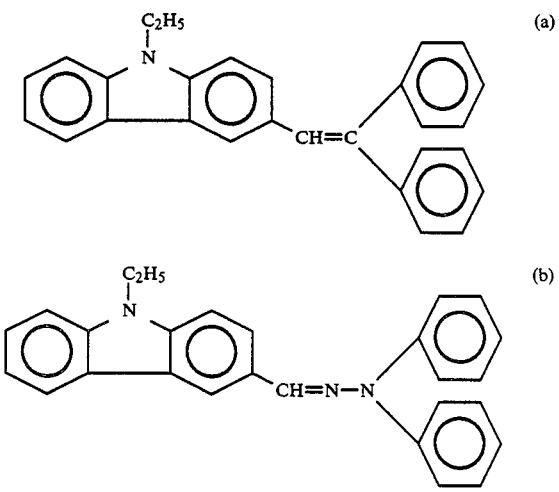

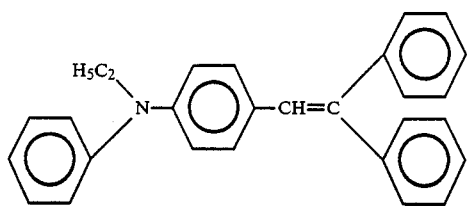

(c)

TABLE 1

| | $V_0$ (V) | $V_1$ (V) | $E_{\frac{1}{2}}$ (lux·sec) | Initial stage (V) | After successive copying of 50000 sheets (V) |
|---|---|---|---|---|---|
| Example 1 | −700 | −690 | 1.8 | $V_D$ −690<br>$V_L$ −100 | −680<br>−110 |
| Comparative example 1 | −690 | −650 | 4.5 | $V_D$ −680<br>$V_L$ −260 | −730<br>−370 |
| Comparative example 2 | −700 | −680 | 2.8 | $V_D$ −680<br>$V_L$ −150 | −650<br>−260 |
| Comparative example 3 | −680 | −650 | 3.4 | $V_D$ −660<br>$V_L$ −200 | −700<br>−330 |

From these results, it can be appreciated that both sensitivity and potential stability of the electrophotographic photosensitive member in which the compound of the present invention is used in the charge transport layer are remarkably more excellent than Comparative examples.

EXAMPLES 2-16

In the respective Examples, in place of the exemplary compound No. (I-6) used as the charge transporting compound in the above Example 1, exemplary compounds (I-1), (I-2), (I-3), (I-4), (I-5), (I-7), (I-10), (I-12), (I-21), (I-22), (I-24), (I-27), (I-30), (I-35) and (I-38) were used and the exemplary pigment II-44 was used as the charge generation substance, and otherwise following the same procedure as in Example 1, electrophotographic photosensitive members were prepared.

The electrophotographic characteristics of the respective photosensitive members were measured according to the same method as in Example 1. The results are shown below.

| Example | Exemplary compound | $E_{\frac{1}{2}}$ (lux·sec) | $V_0$ (−volt) | $V_1$ (−volt) |
|---|---|---|---|---|
| 2 | I-1 | 1.9 | 690 | 680 |
| 3 | I-2 | 3.1 | 660 | 630 |
| 4 | I-3 | 3.5 | 670 | 650 |
| 5 | I-4 | 3.8 | 670 | 640 |
| 6 | I-5 | 3.3 | 650 | 630 |
| 7 | I-7 | 2.5 | 700 | 680 |
| 8 | I-10 | 2.6 | 680 | 660 |
| 9 | I-12 | 1.8 | 690 | 680 |
| 10 | I-21 | 2.1 | 700 | 690 |
| 11 | I-22 | 2.2 | 700 | 680 |
| 12 | I-24 | 2.8 | 680 | 660 |
| 13 | I-27 | 3.3 | 670 | 650 |
| 14 | I-30 | 2.2 | 690 | 680 |
| 15 | I-35 | 2.1 | 690 | 680 |
| 16 | I-38 | 3.0 | 680 | 660 |

| | Initial stage | | After successive copying of 50000 sheets | |
|---|---|---|---|---|
| Example | $V_D$(−volt) | $V_L$(−volt) | $V_D$(−volt) | $V_L$(−volt) |
| 2 | 710 | 100 | 700 | 110 |
| 3 | 680 | 150 | 650 | 170 |
| 4 | 690 | 170 | 660 | 180 |
| 5 | 690 | 190 | 680 | 200 |
| 6 | 680 | 160 | 670 | 170 |
| 7 | 700 | 130 | 680 | 150 |
| 8 | 700 | 130 | 690 | 140 |
| 9 | 690 | 100 | 680 | 110 |
| 10 | 710 | 110 | 690 | 120 |
| 11 | 700 | 110 | 690 | 120 |
| 12 | 690 | 140 | 670 | 160 |
| 13 | 690 | 160 | 670 | 170 |
| 14 | 680 | 110 | 660 | 120 |
| 15 | 690 | 100 | 680 | 110 |
| 16 | 690 | 150 | 660 | 160 |

EXAMPLE 17

100 parts (by weight, hereinafter the same) of electroconductive titanium oxide powder (produced by Titanium Kogyo K.K.), 100 parts of titanium oxide powder (produced by Sakai Kogyo K.K.) and 125 parts of a phenol resin (trade name, Polyphen, produced by Ink K.K.) were mixed in a solvent of 50 parts of methanol and 50 parts of methylcellosolve, followed dispersion in a ball mill for 6 hours. This dispersion was applied on an aluminum cylinder of 60 $\phi \times 260$ mm according to the dip coating method, and thermally cured at 150° C. for 30 minutes to provide an electroconductive layer with a thickness of 20 μm.

Next, on the above electroconductive layer was coated an aqueous ammonia solution of casein (casein 11.2 g, 28% ammonia water 1 g, water 22.2 ml) according to the dip coating method, followed by drying to form a subbing layer with a thickness of 1 μm. Next, 1 part of the exemplary charge generating substance No. II-81, 1 part of a butyral resin (S-LEC BM-2, produced by Sekisui Kagaku K.K.) and 30 parts of isopropyl alcohol were dispersed in a ball mill dispersing machine for 4 hours. The dispersion was coated on the previously formed subbing layer according to the dip coating method, followed by drying to form a charge generation layer. The film thickness was 0.3 μm.

Next, 1 part of the above exemplary compound No. I-6, 1 part of a polysulfone resin (P1700: produced by Union Carbide Co.) and 6 parts of monochlorobenzene were mixed, and dissolved under stirring by a stirrer. This solution was applied on the charge generation layer according to the dip coating method, followed by drying to form a charge transport layer. The film thickness was 12 μm.

The photosensitive member thus prepared was subjected to corona discharging of −5KV. The surface potential at this time was measured (initial potential ($V_0$). Further, the surface potential after leaving this photosensitive member to stand in a dark place for 5 seconds was measured. The sensitivity was evaluated by measuring the dosage necessary for attenuating the potential VK after the dark decay to $\frac{1}{2}$ ($E_{\frac{1}{2}}$ microjoule/cm$^2$). In this measurement, a gallium-/aluminum/arsenic ternary system semiconductor laser (output: 5 mW; oscillation wavelength 780 nm) was used as the light source. The results were as follows.

$V_0$: −710 volt

Potential retentivity: 96%

$$\left(\frac{V_K}{V_O} \times 100\right)$$

$E\frac{1}{2}$: 2.1 microjoule/cm².

Next, the above photosensitive member was set in place of the LBP-CX photosensitive member on a laser beam printer (LBP-CX, produced by Canon) which is an electrophotographic system printer of the reversal development system equipped with the semiconductor laser as described above, and real image forming test was conducted. The conditions are as follows.

Surface potential after primary charging: −700V, surface potential after image exposure: −150V (dosage 2 μJ/cm²), transfer potential: +700V, developer polarity: negative, process speed: 50 mm/sec, developing conditions (developing bias): −450V, image exposure scanning system: image scanning, exposure before primary charging: 50 lux.sec.

Red color whole surface exposure image formation was conducted by line scanning of the laser beam following the letter signals and image signals, whereby good printing was obtained in both letters and images.

EXAMPLE 18

A mixture of 3 g of 4-(4-dimethylaminophenyl)-2,6-diphenylthiapyryliumperchlorate and 5 g of the above Exemplary compound (No. I-6) with 100 ml of a solution of a polyester (Polyester Adhesive 49000, produced by Du Pont) in toluene (50)-dioxane (50) was dispersed in a ball mill for 6 hours. The dispersion was applied on an aluminum sheet with Meyer bar to a film thickness after drying of 15 μm.

The electrophotographic characteristics of the photosensitive member thus prepared were measured according to the same method as in Example 1. The results are shown below.

$V_0$: −690 volt
$V_1$: −680 volt
$E\frac{1}{2}$: 2.2 lux sec
Initial stage
$V_D$: −700 volt
$V_L$: −110 volt
After successive copying of 50000 sheets
$V_D$: −690 volt
$V_L$: −120 volt

EXAMPLE 19

On an aluminum plate, an aqueous ammonia solution of casein (casein 11.2 g, 28% ammonia water 1 g, water 222 ml) was applied with Meyer bar and dried to form a subbing layer with a thickness of 1 μm.

Next, 5 g of the diazo pigment having the following structure (No. II-16):

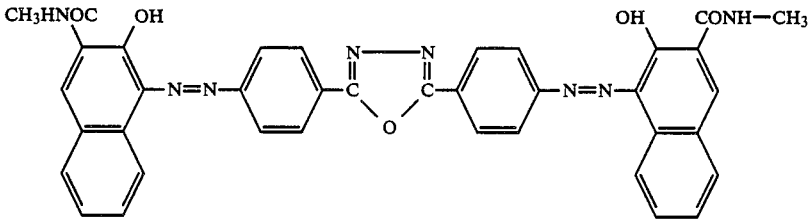

was dispersed together with a solution of 2 g of a butyral resin (butyral formation degree 63 mol%) dissolved in 95 ml of ethanol, the dispersion was applied on the subbing layer to form a charge generation layer with a film thickness after drying of 0.4 μm.

Next, a solution of 5 g of the above exemplary compound (No. I-12) and 5 g of a poly-4,4'-dioxydiphenyl-2,2-propanecarbonate (viscosity average molecular weight 30000) dissolved in 150 ml of dichloromethane was coated on the charge generation layer and dried to form a charge transport layer with a film thickness of 11 μm, thereby preparing an electrophotographic photosensitive member. The electrophotographic characteristics of the electrophotographic photosensitive member thus prepared were measured according to the same method as in Example 1. The results are shown below.

$V_0$: −670 volt
$V_1$: −650 volt
$E\frac{1}{2}$: 2.8 lux sec
Initial stage
$V_D$: −700 volt
$V_L$: −140 volt
After successive copying of 50000 sheets
$V_D$: −690 volt
$V_L$: −670 volt

EXAMPLE 20

A molybdenum plate (substrate) having a thickness of 0.2 mm with its surface being cleaned was fixed at a predetermined position in a glow discharge vapor deposition tank. Next, the tank was internally evacuated to a vacuum degree of about $5 \times 10^{-6}$ Torr. Then, by elevating the input voltage of the heater, the molybdenum substrate temperature was stabilized to 150° C. Then, hydrogen gas and silane gas (15 vol. % based on hydrogen gas) were introduced into the tank to be stabilized to 0.5 Torr by controlling the gas flow rates and the main valve of the vapor deposition tank. Next, a high frequency power of 5 MHz was thrown into the induction coil to generate glow discharging internally of the coil in the tank to provide an input power of 30 W. Under the above conditions, an amorphous silicon film was grown on the substrate and the same conditions were maintained until the film thickness became 2 μm, followed by intermission of glow discharging. Then, with the heating heater and the high frequency power source being turned off, and after the substrate temperature became 100° C., outflow valves for hydrogen gas and silane gas were closed to make the pressure in the tank once to $10^{-5}$ Torr or less. Then, the pressure was returned to atmospheric and the substrate was taken out. Next, on the amorphous silicon layer, except for using the exemplary compound No. I-12 as the charge transporting compound, charge transport layer was formed in entirely the same manner as in Example 1.

The photosensitive member thus obtained was set in a charging exposure experimental device and subjected to corona charging of −6KV, followed immediately by irradiation of a light image. The light image was irradiated through a transmission type test charge by use of a tungsten lamp light source. Immediately thereafter, ⊕ chargeable developer (containing toner and carrier) was cascaded on the surface of the photosensitive member, whereby a good toner image was obtained on the surface of the photosensitive member.

EXAMPLE 21

After 3 g of 4-(4-dimethylaminophenyl)-2,6-diphenyl-thiapyryliumperchlorate and 3 g of poly(4,4'-isopropyridenediphenylenecarbonate) were thoroughly dissolved in 200 ml of dichloromethane, 100 ml of toluene was added to precipitate an amorphous complex. The precipitate was filtered off and then redissolved with addition of dichloromethane, followed by addition of 100 ml of n-hexane to the solution to obtain a precipitate of an amorphous complex.

The amorphous complex (5 g) was added to 95 ml of a methanol solution containing 2 g of a polyvinylbutyral and the mixture was dispersed in a ball mill for 6 hours. The dispersion was applied on an aluminum plate having a casein layer with Meyer bar to a film thickness after drying of 0.4 μm to form a charge generation layer.

Next, on the charge generation layer was formed a coated layer of a charge transport layer in entirely the same manner as in Example 1 except for using the exemplary compound No. I-30.

The electrophotographic characteristics of the photosensitive member thus prepared were measured according to the same method as in Example 1. The results are shown below.

$V_0$: −690 volt
$V_1$: −680 volt
$E_{\frac{1}{2}}$: 2.5 lux sec
Initial stage
$V_D$: −700 volt
$V_L$: −120 volt
After successive copying of 50000 sheets
$V_D$: −690 volt
$V_L$: −140 volt

EXAMPLE 22

The same amorphous complex as used in Example 21 (5 g) and 5 g of the above exemplary compound No. I-36 were added into 150 ml of a tetrahydrofuran solution of a polyester (Polyester Adhesive 49000, produced by Du Pont Co.), followed by thorough mixing under stirring. The mixture was coated on an aluminum sheet with Meyer bar to a film thickness after drying of 15 μm.

The electrophotographic characteristics of this photosensitive member were measured according to the same method as in Example 1. The results are shown below.

$V_0$: −700 volt
$V_1$: −690 volt
$E_{\frac{1}{2}}$: 2.8 lux sec
Initial stage
$V_D$: −710 volt
$V_L$: −140 volt
After successive copying of 50000 sheets
$V_D$: −700 volt
$V_L$: −150 volt

What we claim is:

1. An electrophotographic photosensitive member comprising a charge generating material and a charge transport material containing a compound represented by the formula (1) shown below:

wherein A represents 1,2-, 2,3- or 3,4-benzocarbazolyl group; $R_1$, $R_2$ and $R_3$, which may be the same or different, each represent hydrogen atom, alkyl group, aralkyl group, aryl group or heterocyclic group, with proviso that $R_2$ and $R_3$ cannot be hydrogen atoms at the same time.

2. An electrophotographic photosensitive member according to claim 1 comprising a layer containing a compound represented by the formula (2) which is a compound represented by the above formula (1) wherein A is 1,2-benzocarbazolyl group:

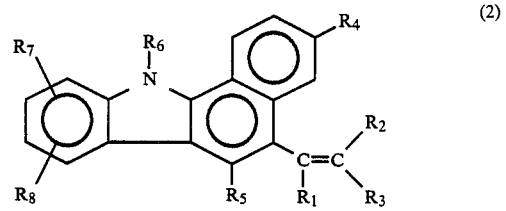

wherein $R_1$, $R_2$, $R_3$ and $R_6$, which may be the same or different, each represent hydrogen atom, alkyl group, aralkyl group, aryl group or heterocyclic group, with proviso that $R_2$ and $R_3$ cannot be hydrogen atoms at the same time; $R_4$, $R_5$, $R_7$ and $R_8$, which may be the same or different, each represent hydrogen atom, alkyl group, alkoxy group, halogen atom-substituted amino group or alkylthio group.

3. An electrophotographic photosensitive member according to claim 2 comprising a layer containing a compound of the formula (3) which is a compound represented by the above formula (2) wherein $R_2$ and $R_3$ are phenyl groups:

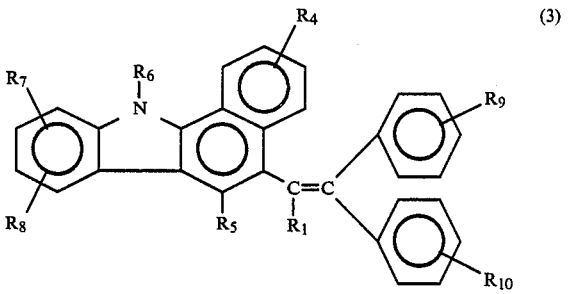

wherein $R_1$, $R_4$, $R_5$, $R_6$, $R_7$ and $R_8$ are the same as in the above formula (2); $R_9$ and $R_{10}$, which may be the same or different, each represent hydrogen atom, alkyl group, alkoxy group, halogen atom, substituted amino group or alkylthio group.

4. An electrophotographic photosensitive member according to claim 1, wherein said electrophotographic photosensitive member has a laminated structure of a charge generation layer and a charge transport layer.

5. An electrophotographic photosensitive member according to claim 4, wherein the layer containing the compound represented by the formula (1) is a charge transport layer.

6. An electrophotographic photosensitive member according to claim 5, wherein said charge transport layer is laminated on the charge generation layer.

7. An electrophotographic photosensitive member according to claim 4, wherein said charge transport layer has a thickness of 5 $\mu$m to 30 $\mu$m.

8. An electrophotographic photosensitive member according to claim 5, wherein the formulation proportion of the compound represented by the formula (1) and the binder in said charge transport layer are 10 to 500 parts by weight per 100 parts by weight of the binder.

9. An electrophotographic photosensitive member according to claim 4, wherein said charge generation layer contains a compound selected from $\beta$-type copper phthalocyanine, azo pigments and amorphous complexes.

10. An electrophotographic photosensitive member according to claim 4, wherein said charge generation layer is an amorphous silicon layer.

11. An electrophotographic photosensitive member according to claim 4, wherein said charge generation layer has a thickness of 5 $\mu$m or less.

12. An electrophotographic photosensitive member according to claim 11, wherein said charge generation layer has a thickness of 0.001 $\mu$m to 1 $\mu$m.

* * * * *

UNITED STATES PATENT AND TRADEMARK OFFICE
CERTIFICATE OF CORRECTION

PATENT NO. : 4,798,777
DATED : January 17, 1989
INVENTOR(S) : TAKAO TAKIGUCHI, ET AL.

It is certified that error appears in the above-identified patent and that said Letters Patent is hereby corrected as shown below:

IN [54] TITLE

"BENZOCARAZOLE" should read --BENZOCARBAZOLE--.

COLUMN 1

Line 2, "BENZOCARAZOLE" should read --BENZOCARBAZOLE--.

COLUMN 20

Line 22, "$V_L$:-670 volt" should read --$V_L$:-160 volt--.

Signed and Sealed this

Fourteenth Day of November, 1989

Attest:

JEFFREY M. SAMUELS

Attesting Officer     Acting Commissioner of Patents and Trademarks